US 6,372,914 B1

United States Patent
Suzuki et al.

(10) Patent No.: US 6,372,914 B1
(45) Date of Patent: Apr. 16, 2002

(54) INTERMEDIATES USEFUL FOR THE MANUFACTURE OF CARBAPENEM AND A STEREOSELECTIVE MANUFACTURING METHOD THEREFOR

(75) Inventors: Takaaki Suzuki, Tokyo; Isao Sugiyama, Ibaraki; Manabu Sasho, Ibaraki; Nobuaki Sato, Ibaraki; Atsushi Kamada, Ibaraki; Kazuhide Ashizawa, Ibaraki, all of (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/705,183

(22) Filed: Nov. 2, 2000

Related U.S. Application Data

(62) Division of application No. 09/423,825, filed as application No. PCT/JP98/02225 on May 21, 1998.

(30) Foreign Application Priority Data

May 23, 1997  (JP) .............................................. 9-133171

(51) Int. Cl.⁷ ...................... C07D 263/18; C07D 207/04
(52) U.S. Cl. ...................... 548/225; 548/110; 548/225; 548/146; 548/518
(58) Field of Search ................................ 548/182, 215, 548/225, 518, 523, 110, 109, 146

(56) References Cited

U.S. PATENT DOCUMENTS 6,037,341 A * 3/2000 Sato et al. .................. 514/210

FOREIGN PATENT DOCUMENTS

WO 97/102555 * 3/1997

OTHER PUBLICATIONS

"ER–35786" Drugs of the Future, Barcelona, Es, vol. 21, No. 4, 1996, pp 361–365 XP–000917207.

* cited by examiner

*Primary Examiner*—Alan L. Rotman
*Assistant Examiner*—Rita Desai
(74) *Attorney, Agent, or Firm*—Flynn, Thiel, Boutell & Tanis, P.C.

(57) ABSTRACT

The present invention provides an efficient stereoselective method for manufacturing (2S,4S)-2-[[(R)-hydroxy-(3R)-cyclic amine-3-yl]methyl]pyrrolidine-4-thiol or a salt thereof which is useful as an intermediate for the manufacture of carbapenem and also provides the intermediate.

A method for manufacturing which comprises the step of reacting a compound of the formula (I):

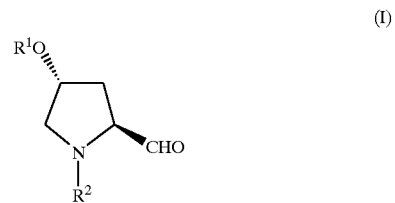

(I)

(wherein, $R^1$ is a lower alkylsulfonyl group, an optionally substituted arylsulfonyl group or an alkylsilyl group; and $R^2$ is a protecting group for an amino group) with a compound of the formula (II):

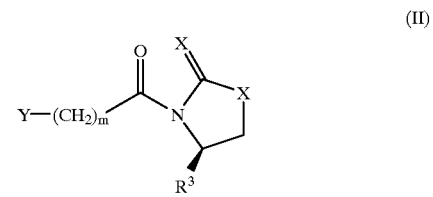

(II)

(wherein, $R^3$ is a substituted or unsubstituted lower alkyl group or aryl group; X is an oxygen atom or a sulfur atom; Y is an azide group or a nitro group; and m is an integer of 2 to 5).

4 Claims, No Drawings

INTERMEDIATES USEFUL FOR THE MANUFACTURE OF CARBAPENEM AND A STEREOSELECTIVE MANUFACTURING METHOD THEREFOR

This is a division of Ser. No. 09/423 825, filed Nov. 12, 1999 which is a 371 of PCT JP/9802225/ filed May 21, 1998.

FIELD OF THE INVENTION

The present invention relates to intermediates useful for the manufacture of carbapenem compound useful as antibacterial agents and also to a method for manufacturing the same.

PRIOR ART

With regard to antibiotics of a carbapenem series, synthetic studies for many compounds have been carried out since the discovery of thienamycin in 1976. Recently, there are many studies on carbapenem compounds having a 2-substituted pyrrolidine-4-thio group at the 2-position of a carbapenem skeleton and, among them, there is a disclosure on the following carbapenem compounds having an excellent antibacterial activity to *Pseudomonas aeruginosa* in Drugs of the Future, 1996, 21(4):361–365.

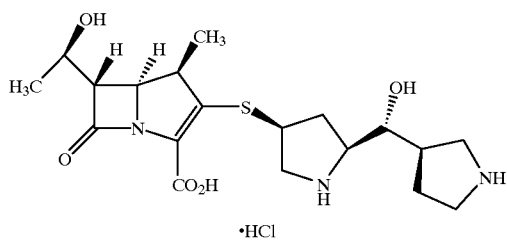

·HCl

In addition, compounds related thereto are disclosed in JP-A 8-73462 etc.

Manufacture of the carbapenem compounds described in those reports are carried out by a condensation of a reactive compound of a carbapenem skeleton with an optically active pyrrolidine-4-thiol compound (VIII):

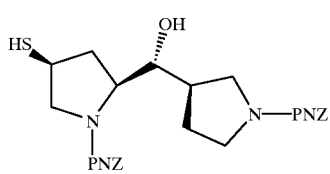

(VIII)

(wherein, PNZ is a p-nitrobenzyloxycarbonyl group), and the optically active pyrrolidine-4-thiol compound (VIII) is manufactured according to the steps as shown in the following reaction formulae:

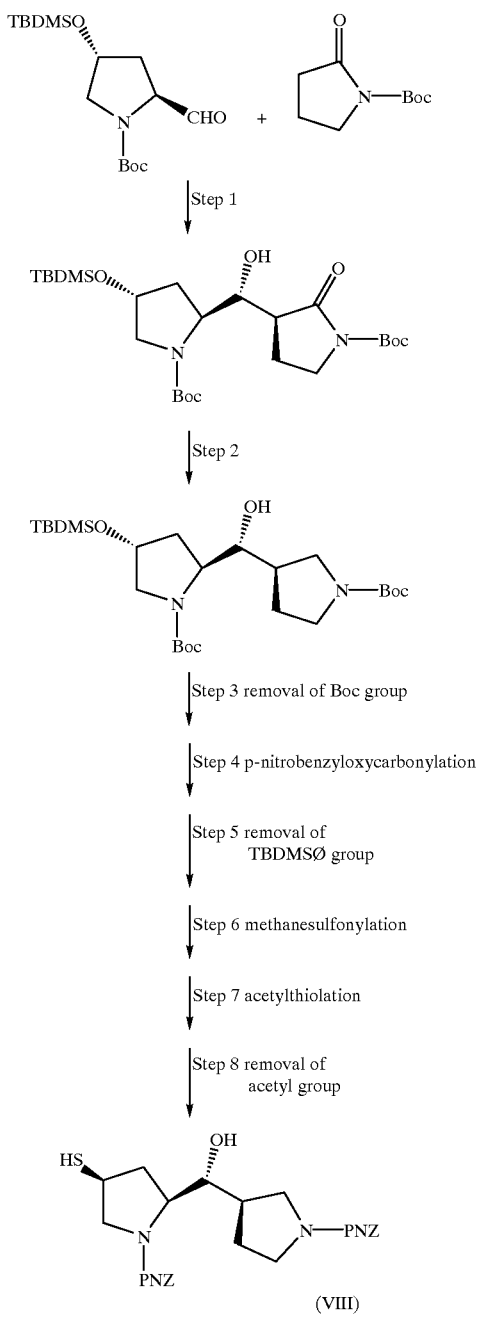

(wherein, Boc is a tert-butoxycarbonyl group, PNZ is a p-nitrobenzyloxycarbonyl group and TBDMS is a tert-butyldimethylsilyl group.)

However, according to the disclosed method, a diastereomer having the unnecessary configuration is also obtained in the first step and, therefore, there is the following industrial disadvantage judging from preparing the diastereomer having the desired configuration only. Thus, 1) the diastereomer having the unnecessary configuration is to be separated and removed; and 2) yield of the diastereomer having the desired configuration is low.

DISCLOSURE OF THE INVENTION

An object of the present invention is to overcome the above disadvantages or, in other words, to manufacture only the diastereomer having the desired configuration selectively and in a high yield.

As a result of an intensive investigation, the present inventors have found that the method for the manufacture of stereoselective pyrrolidine-4-thiol compounds as mentioned below is able to solve the above problems and have accomplished the present invention.

Namely, the present invention is a method for the manufacture of (2S,4S)-2-[[(R)-hydroxy-(3R)-cyclic amine-3-yl]methyl]pyrrolidine-4-thiol represented by the formula (II):

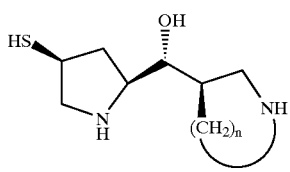

(II)

(wherein, n is an integer of 1 to 4) or a salt thereof, which comprises the steps of treating a (2S,4R)-pyrrolidine-2-carbaldehyde compound represented by the formula (III):

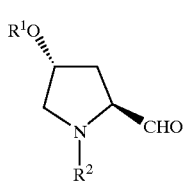

(III)

(wherein, R¹ is a lower alkylsulfonyl group, an optionally substituted arylsulfonyl group or an alkylsilyl group; and R² is a protecting group for an amino group) with a (4R)-3-(ω-substituted alkanoyl)oxazolidin-2-one (or thiazolidin-2-thione) compound represented by the formula (IV):

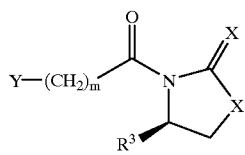

(IV)

(wherein, R³ is a substituted or unsubstituted lower alkyl group or an aryl group; X is an oxygen atom or a sulfur atom; Y is an azide group or a nitro group; and m is an integer of 2 to 5) to give a (4R)-[3-[2-(ω-substituted alkyl)-3-(R)-hydroxy-1-oxo-3-(2S,4R)-2-pyrrolidinyl]propyl]oxazolidin-2-one (or thiazolidin-2-thione) compound represented by the formula (I):

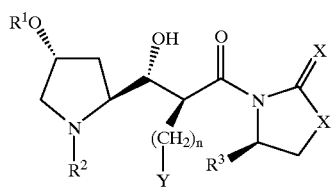

(I)

(wherein, R¹ is a lower alkylsufonyl group, an optionally substituted arylsulfonyl group or an alkylsilyl group; R² is a protecting group for an amino group; R³ is a substituted or unsubstituted lower alkyl group or an aryl group; X is an oxygen atom or a sulfur atom; Y is an azide group or a nitro group; and n is an integer of 1 to 4); reducing the azide group or the nitro group thereof to give a (3S)-[[(R)-hydroxy-(2S,4R)-2-pyrrolidinyl]methyl]lactam compound represented by the formula (V):

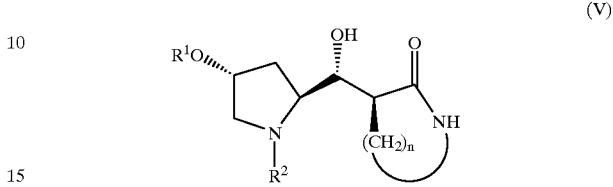

(V)

(wherein, R¹ is a lower alkylsulfonyl group, an optionally substituted arylsulfonyl group or an alkylsilyl group; R² is a protecting group for an amino group; and n is an integer of 1 to 4); reducing the carbonyl group therein with or without protecting the NH group of the resulting cyclic amide to give a (2S,4R)-2-[[(R)-hydroxy-(3R)-cyclic amine-3-yl]methyl]pyrrolidine compound represented by the formula (VI):

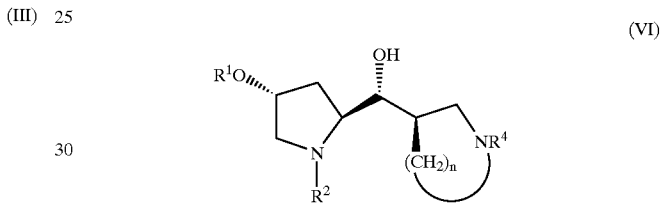

(VI)

(wherein, R¹ is a lower alkylsulfonyl group, an optionally substituted arylsulfonyl group or an alkylsilyl group; R² is an protecting group for an amino group; R⁴ is a hydrogen atom or a protecting group for an amino group; and n is an integer of 1 to 4); when R¹ is an alkylsilyl group, eliminating the alkylsilyl group selectively, followed by converting to a lower alkylsulfonyl group or an optionally substituted arylsulfonyl group and making it into an acylthio group to give a (2S,4S)-2-[[(R)-hydroxy-(3R)-cyclic amine-3-yl]methyl]-4-acylthiopyrrolidine compound represented by the formula (VII):

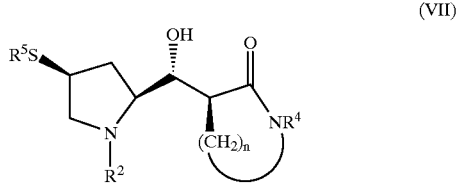

(VII)

(wherein, R² is a protecting group for an amino group; R⁴ is a hydrogen atom or a protecting group for an amino group; R⁵ is an acyl group; and n is an integer of 1 to 4); and then eliminating the protecting group(s). Further, the present invention relates to novel intermediates, i.e. a (4R)-[3-[2-(ω-substituted alkyl)-3-(R)-hydroxy-1-oxo-3-(2S,4R)-2-pyrrolidinyl]propyl]oxazolidin-2-one (or thiazolidine-2-thione) compound and (2S,4S)-2-[[(R)-hydroxy-(3R)-cyclic amine-3-yl]methyl]pyrrolidin-4-thiol or salts thereof.

A (2S,4S)-2-[[(R)-hydroxy-(3R)-cyclic amine-3-yl]methyl]pyrrolidin-4-thiol, which is a novel intermediate, is capable of forming a salt in the presence of an acid and it goes without saying that such a salt is also covered by the present invention. Examples of the salt include hydrochloride, hydrobromide, hydroiodide, sulfate, nitrate, phosphate, trifluoroacetate and sulfonates such as methanesulfonate, p-toluenesulfonate, etc.

In the present invention, examples of the lower alkylsulfonyl group found in the definition for $R^1$ include a methylsulfonyl group, an ethylsulfonyl group, a propylsulfonyl group, etc.; examples of the arylsulfonyl group found therein include a phenylsulfonyl group, a p-toluenesulfonyl group, etc.; and examples of the alkylsilyl group found in the definition for $R^1$ include a trimethylsilyl group, a triethylsilyl group, an isopropyldimethylsilyl group, an tert-butyldimethylsilyl group, a tert-butyldiphenylsilyl group, a vinyldimethylsilyl group, etc.

Examples of the protecting group for an amino group found in the definitions of $R^2$ and $R^4$ include substituted or unsubstituted lower alkanoyl groups such as a formyl group, an acetyl group, a chloroacetyl group, a dichloroacetyl group, a propionyl group, a phenylacetyl group, a thienylacetyl group, etc., or substituted or unsubstituted lower alkoxycarbonyl groups such as a tert-butoxycarbonyl group, a benzyloxycarbonyl group, a p-nitrobenzyloxycarbonyl group, a p-methoxybenzyloxycarbonyl group, a p-bromobenzyloxycarbonyl group, a 2,4-dichlorobenzyloxycarbonyl group, etc.

Examples of the substituted or unsubstituted lower alkyl group found in the definition of $R^3$ include a methyl group, an ethyl group, an isopropyl group, a benzyl group, etc., while an example of the aryl group found therein include a phenyl group, etc.

Examples of the acyl group found in the definition of $R^5$ include the groups derived from saturated or unsaturated fatty acids such as a formyl group, an acetyl group, a propionyl group, an acryloyl group, etc., the groups derived from carbocyclic carboxylic acids such as a cyclohexylcarbonyl group, a benzoyl group, a toluoyl group, a cinnamoyl group etc., the groups derived from heterocyclic carboxylic acids such as a nicotinoyl group, a thenoyl group etc., a morpholinylacetyl group, a thiomorpholinylacetyl group, etc.

DETAILED DESCRIPTION OF THE INVENTION

The manufacturing method according to the present invention will be described in more detail as follows.

(wherein, $R^1$ is a lower alkylsulfonyl group, an optionally substituted arylsulfonyl group or an alkylsilyl group; $R^2$ is a protecting group for an amino group; $R^3$ is a substituted or unsubstituted lower alkyl group or an aryl group; $R^4$ is a hydrogen atom or a protecting group for an amino group; $R^5$ is an acyl group; X is an oxygen atom or a sulfur atom; Y is an azide group or a nitro group; m is an integer of 2 to 5; and n is an integer of 1 to 4.)

(Step A)

This step is that where a (4R)-[3-[2-(ω-substituted alkyl)-3-(R)-hydroxy-1-oxo-3-(2S,4R)-2-pyrrolidinyl]propyl] oxazolidin-2-one (or thiazolidine-2-thione) compound having a desired configuration is selectively manufactured by means of an asymmetric aldol reaction by the reaction of a (2S,4R)-pyrrolidine-2-carbaldehyde compound with (4R)-3-(ω-substituted alkanoyl)oxazolidin-2-one (or thiazolidine-2-thione) compound in an aprotic solvent in the presence of a base. Examples of the base include n-butyl lithium (n-BuLi), lithium diisopropylamide (LDA), lithium bis (trimethylsilyl)amide (LHMDS), sodium bis(trimethylsilyl) amide (NaHMDS) etc. and, among them, lithium bis(trimethylsilyl)amide, (LHMDS) is particularly preferred. Examples of the aprotic solvent include diethyl ether, tetrahydrofuran (THF), dioxane, 1,2-dimethyl-2-imidazolidinone (DMI), dimethylacetamide (DMA), dimethylformamide (DMF), dimethyl sulfoxide (DMSO), etc. The reaction is carried out at from −40° C. to −100° C.

(Step B)

This step is that where an azide group or a nitro group of a (4R)-[3-[2-(ω-substituted alkyl)-3-(R)-hydroxy-1-oxo-3-(2S,4R)-2-pyrrolidinyl]propyl]oxazolidin-2-one (or thiazolidine-2-thione) compound is reduced and, at the same time, an oxazolidinyl group or a thiazolidinyl group is eliminated whereupon a lactam ring is formed. The reduction is carried out by means of a catalytic reduction using palladium-carbon, platinum oxide catalyst, etc. or using sodium borohydride. Although there is no particular limitation for the solvent in the catalytic reduction, the use of tetrahydrofuran (THF) is preferred. When sodium borohydride is used, the use of an alcoholic solvent, particularly isopropyl alcohol, is preferred.

An optically active oxazolidin-2-one compound or thiazolidine-2-thione compound which is produced in this reaction is recovered and is recycled in the manufacture the of (4R)-3-(ω-substituted alkanoyl)oxazolidin-2-one (or thiazolidine-2-thione) compound.

(Step C)

This step is that where a carbonyl group of the lactam compound produced in the step B is reduced to give a cyclic amine compound. The reduction is carried out with or without protecting the NH group of the lactam ring. Examples of the reducing agent used here include aluminum reducing agents such as aluminum hydride, lithium aluminum hydride, lithium trimethoxyaluminohydride, etc.; diborane; and borane complexes such as a dimethyl sulfide-borane complex, a trimethylamine-borane complex in the presence of a Lewis acid and, among them, a dimethyl sulfide-borane complex is preferred. Examples of the reaction solvent include those which do not participate in the reaction such as tetrahydrofuran (THF), dioxane, diglyme (DGM), etc. Protection of the NH group in the lactam ring is carried out by an acid chloride such as acetyl chloride, benzoyl chloride, etc., an acid anhydride such as acetic anhydride, etc., a substituted lower alkyloxycarbonyl halogenide such as p-nitrobenzyloxycarbonyl chloride, etc., or di-tert-butyl dicarbonate, etc. in the presence of a base such as dimethylaminopyridine, etc. in a solvent such as acetone, acetonitrile, tetrahydrofuran (THF), dioxane, etc.

(Step D)

This step is that where a lower alkylsulfonyloxy group or an optionally substituted arylsulfonyl group at the 4-position in an R-configuration in a pyrrolidine ring of (2S,4R)-2-[[(R)-hydroxy-(3R)-cyclic amine-3-yl]methyl]pyrrolidine compound (when $R^1$ is an alkylsilyl group, the alkylsilyl group is selectively eliminated and converted to a lower alkylsulfonyl group or an optionally substituted arylsulfonyl group) is converted to an acylthio group in an S-configuration. The reaction is carried out either with a thiocarboxylate such as potassium thioacetate or sodium thioacetate in a polar solvent such as acetonitrile, acetone, 1,2-dimethyl-2-imidazolidinone (DMI), dimethylacetamide (DMA), dimethylformamide (DMF), dimethyl sulfoxide (DMSO), etc., or with a thiocarboxylic acid such as thioacetic acid, thiobenzoic acid, etc., in the presence of a base such as potassium carbonate, cesium carbonate, etc.

(Step E)

This step is that where an acyl group in an acylthio group of a (2S,4S)-2-[[(R)-hydroxy-(3R)-cyclic amine-3-yl]methyl]-4-acylthiopyrrolidine compound and a protecting group for an amino group on a pyrrolidine ring is, and, if an amino group on another cyclic amine ring has a protecting group, this protecting group is also, eliminated. The reaction is carried out in an alcoholic solvent such as methanol, ethanol etc., or tetrahydrofuran (THF) or dioxane in the presence of a mineral acid such as hydrochloric acid, sulfuric acid, etc. The reaction may also be carried out by treating with an aqueous solution of sodium hydroxide, potassium hydroxide or lithium hydroxide in the above-mentioned solvent. Further, when a protecting group for the amino group is a reductively eliminated group such as a benzyloxycarbonyl group, a nitrobenzyloxycarbonyl group etc., it is also possible that the protecting group is firstly eliminated by means of reduction and then the acyl group in the acylthio group is eliminated by the above-mentioned acid or alkali.

EXAMPLES

As hereunder, Examples will be given for making the understanding of the present invention easier, although it goes without saying that the present invention is not limited thereto. Incidentally, prior to giving Examples, Production Examples for the compounds which are the materials for the manufacturing method of the present invention will be mentioned. Further, the usefulness of the method of the present invention will be shown by means of Referential Example 1.

Production Example 1

(4R)-3-(4-Azidobutanoyl)-4-phenyloxazolidin-2-one

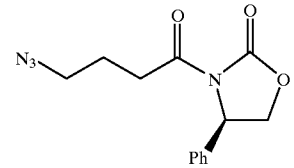

A catalytic amount of dimethylformamide was added to a solution of 4-azidobutyric acid (10.3 g, 80.0 mM) in 100 ml of methylene chloride and, thereafter, thionyl chloride (8.7 ml, 119.5 mM) was added dropwise thereto under ice-cooling. After stirring the reaction mixture at room temperature for one hour, it was evaporated to give a crude acid chloride.

A 1.6 M solution of n-butyl lithium in hexane (40.2 ml, 64.3 mM) was added dropwise into a solution of (4R)-4-phenyl-2-oxazolidinone (manufactured by Aldrich; 10 g, 61.3 mM) in tetrahydrofuran (80 ml) at −78° C. and the mixture was stirred at the same temperature for 30 minutes. A solution of the previously synthesized acid chloride in tetrahydrofuran (100 ml) was slowly added dropwise into the reaction mixture and the mixture was further stirred for 30 minutes. The reaction was ceased by adding dropwise a saturated aqueous solution of sodium bicarbonate into the reaction mixture followed by warming up to room temperature. The mixture was poured into water followed by extracting with ethyl acetate and the organic layer was washed with a saturated aqueous solution of sodium bicarbonate, water and brine in this order and dried over anhydrous magnesium sulfate. The solvent was removed and the residue was subjected to a silica gel column chromatography (hexane/ethyl acetate=5/1) to give the title compound (17 g, 99%).

$^1$H-NMR (CDCl$_3$) δ: 1.84(2H,quint,J=7 Hz), 2.88(2H,t, J=7 Hz), 3.25(2H,t,J=7 Hz), 4.24(1H,dd,J=4,9 Hz), 4.65(1H, t,J=7 Hz), 5.36(1H,dd,J=4,9 Hz), 7.22–7.35(5H,m)

Production Example 2

Methyl (2S,4R)-N-tert-butoxycarbonyl-4-methanesulfonyloxypyrrolidine-2-carboxylate

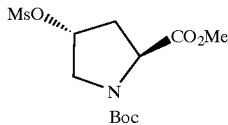

Triethylamine (14.8 ml, 106.0 mM) and methanesulfonyl chloride (6.9 ml, 90.0 mM) were added to a solution of methyl (2S,4R)-N-tert-butoxycarbonyl-4-hydroxypyrrolidine-2-carboxylate (20 g, 81.5 mM) in anhydrous tetrahydrofuran (200 ml) under ice-cooling in a nitrogen gas stream, and the mixture was stirred for 30 minutes. The reaction mixture was poured into water followed by extracting with ethyl acetate, the organic layer was washed with a saturated aqueous solution of ammonium chloride, a saturated aqueous solution of sodium bicarbonate, water and brine in this order and dried over anhydrous magnesium sulfate and the solvent was removed to give the title compound almost quantitatively (27 g).

$^1$H-NMR (CDCl$_3$) δ: 1.42(5H,s), 1.47(4H,s), 2.22–2.31 (1H,m), 2.54–2.61(1H,m), 3.07(3H,s),3.73–3.90(5H,m), 4.43(1H,td,J=7,28 Hz), 5.25–5.30(1H,m)

Production Example 3

(2S,4R)-N-tert-Butoxycarbonyl-4-methanesulfonyloxy-2-hydroxymethylpyrrolidine

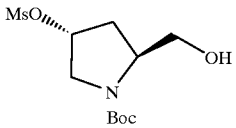

Lithium borohydride (3.6 g, 163.0 mM) was added to a solution of methyl (2S,4R)-N-tert-butoxycarbonyl-4-methanesulfonyloxypyrrolidine-2-carboxylate (26.5 g, 81.5 mM) in anhydrous tetrahydrofuran (300 ml) with ice-cooling in a nitrogen gas stream and the mixture was stirred at room temperature for 3 hours. The reaction mixture was ice-cooled again, the reaction was ceased by adding dropwise a saturated aqueous solution of ammonium chloride carefully and the solvent was removed. The residue was poured into water, the insoluble matters were dissolved using 1N hydrochloric acid, the mixture was extracted with ethyl acetate and the organic layer was washed with 1N hydrochloric acid, water, a saturated aqueous solution of sodium bicarbonate, water and brine in this order and dried over anhydrous magnesium sulfate. The solvent was removed to give the title compound almost quantitatively (24 g).

$^1$H-NMR (CDCl$_3$) δ: 1.48(9H,s), 1.82–1.95(1H,m), 2.32–2.42(1H,m) 3.06(3H,s), 3.56(2H,dd,J=6,12 Hz), 3.74–3.90(2H,m), 4.20–4.48(1H,m), 5.15–5.24(1H,m)

Production Example 4

(2S,4R)-N-tert-Butoxycarbonyl-4-methanesulfonyloxypyrrlidine-2-carbaldehyde

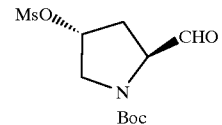

A solution of dimethyl sulfoxide (4.2 ml, 59.3 mM) in anhydrous methylene chloride (20 ml) was added dropwise into a solution of oxalyl chloride (3.5 ml, 40.3 mM) in anhydrous methylene chloride (100 ml) at −70° C. in a nitrogen gas stream and the mixture was stirred for 20 minutes. A solution of (2S,4R)-N-tert-butoxycarbonyl-4-methanesulfonyloxy-2-hydorxymethylpyrrolidine (7 g, 23.7 mM) in anhydrous methylene chloride (20 ml) was added dropwise and the mixture was further stirred for 20 minutes. After adding dropwise triethylamine (11.6 ml, 83.0 mM) thereto, the mixture was warmed up to room temperature. The reaction mixture was poured into water and the organic layer was washed with a 10% aqueous solution of citric acid, water, a saturated aqueous solution of sodium carbonate and brine in this order and dried over anhydrous magnesium sulfate. After removing the solvent, the resulting solid matter was washed with hexane to give the title compound (6.5 g, 93%).

$^1$H-NMR (CDCl$_3$) δ: 1.45(4.5H,s), 1.49(4.5H,s), 2.10–2.21(1H,m), 2.44(0.5H,q,J=7 Hz), 2.55(0.5H,q,J=7 Hz), 3.07(3H,s),3.70(1H,dd,J=4,13 Hz), 3.84(0.5H,bd,J=13 Hz), 3.95(0.5H,bd,J=13 Hz), 4.27–4.33(0.5H,m), 4.38–4.47 (0.5H,m),5.22–5.32(1H,m), 9.47(0.6H,d,J=4 Hz), 9.59 (0.4H,d,J=2 Hz)

Example 1

(4R)-3-[(2S, 3R)-2-Azidoethyl-3-[(2S,4R)-N-tert-butoxycarbonyl-4-tert-butyldimethylsilyloxypyrrolidin-2-yl]-3-hydroxy-1-oxopropyl]-4-phenyloxazolidin-2-one

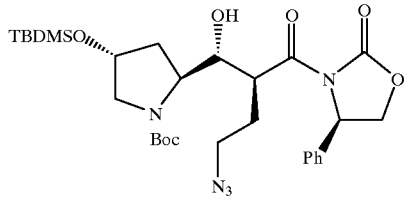

A 1.0 M solution of lithium bis(trimethylsilyl)amide (LHMDS) in tetrahydrofuran (10 ml, 10.0 mM) was added dropwise into a solution of (4R)-3-(4-azidobutanoyl)-4-phenyloxazolidin-2-one (2.5 g, 9.1 mM) in tetrahydrofuran (50 ml) at −70° C. in a nitrogen gas stream and the mixture was stirred at the same temperature for one hour. Then, a solution of (2S,4R)-N-tert-butoxycarbonyl-4-tert-butyldimethylsilyloxypyrrolidine-2-carbaldehyde (3.6 g, 10.9 mM) in tetrahydrofuran (15 ml) was added dropwise into the reaction mixture and then stirred at the same temperature for 40 minutes. The reaction was ceased by adding dropwise a solution of acetic acid (1.1 g, 18.3 mM) in tetrahydrofuran (5 ml) thereto. The mixture was poured into a 10% aqueous solution of citric acid followed by extracting with ethyl acetate, and the organic layer was washed with a 10% aqueous solution of citric acid, water, a saturated aqueous solution of sodium bicarbonate, water and brine in this order and dried over anhydrous magnesium sulfate.

The solvent was removed and the residue was subjected to a silica gel column chromatography (Wakogel C-200; hexane/ethyl acetate=4/1) to give the title compound (4.0 g, 72%).

$^1$H-NMR (CDCl$_3$) δ: 0.08(6H,s), 0.81(9H,s),1.38(9H,s), 1.60– 2.30(5H,m), 2.98(0.5H,t,J=8 Hz), 3.17(1H,dd,J=5,12 Hz), 3.27(0.5H,t,J=8 Hz), 3.20–3.66(2H,m), 3.90–4.32(3H, m), 4.76(1H,dd,J=6,9 Hz), 4.60–4.68(1H,m), 5.34–5.44(1H, m), 7.22–7.38 (5H,m)

Example 2

(3S)-3-[[(R)-Hydroxy-(2S,4R)-(N-tert-bytoxycarbonyl-4-tert-bytyldimethylsilyloxy) pyrrolidin-2-yl]methyl]-pyrrolidin-2-one

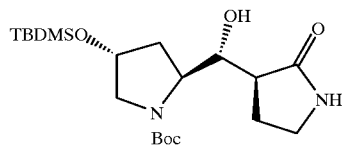

A 10% palladium-carbon (1.9 g) was added to a solution of (4R)-3-[[(2S,3R)-2-azidoethyl-3-{(2S,4R)-N-tert-butoxycarbonyl-4-tert-butyldimethylsilyloxypyrrolidin-2-yl}-3-hydroxy-1-oxopropyl]-4-phenyloxazolidin-2-one (3.8 g, 6.3 mM) in tetrahydrofuran (50 ml), and the mixture was subjected to a catalytic hydrogen reduction at room temperature and 4 atmospheres pressure for 1 hour and 40 minutes. The reaction mixture was filtered through Celite and the filtrate was concentrated.

The residue was subjected to a silica gel column chromatography (Wakogel C-200; hexane/ethyl acetate=1/2) to give the title compound as colorless needles (2.32 g, 87%).

$^1$H-NMR (CDCl$_3$) δ: 0.08(6H,s), 0.81(9H,s), 1.40(9H,s), 1.60–1.74(1H,m), 1.75–2.27(4H,m), 3.22–3.35(3H,m), 3.36–3.43(1H,m), 3.78–3.80(0.3H,m), 3.87–3.94(0.7H,m), 4.05– 4.13(0.3H,m), 4.18–4.25(0.7H,m), 4.45–4.55(1H,m), 6.02(0.7H,m), 6.22(0.3H,m)

Example 3

(3S)-N-tert-Butoxycarbonyl-3-[[(R)-hydroxy-(2S, 4R)-(N-tert-bytoxycarbonyl-4-tert-butyldimethylsilyloxy)-pyrrolidin-2-yl]methyl] pyrrolidin-2-one

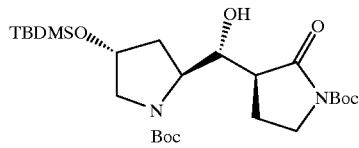

4-Dimethylaminopyridine (275 mg, 2.3 mM) and di-tert-butyl dicarbonate (517 mg, 2.5 mM) were added to a solution of (3S)-3-[[(R)-hydroxy-(2S,4R)-(N-tert-butoxycarbonyl-4-tert-butyldimethylsilyloxy)pyrrolidin-2-yl]methyl]pyrrolidin-2-one (850 mg, 2.1 mM) in a 1:1 mixture (10 ml) of methylene chloride and acetonitrile followed by stirring at room temperature for 5 hours. The mixture was poured into water followed by extracting with ethyl acetate and the organic layer was washed with a saturated aqueous solution of ammonium chloride and brine in this order and dried over anhydrous magnesium sulfate. The solvent was removed and the residue was subjected to a silica gel column chromatography (Wakogel C-200; hexane/ethyl acetate=5/1) to give the title compound (874 mg, 83%).

$^1$H-NMR (CDCl$_3$) δ: 0.08(6H,s), 0.87(9H,s), 1.45(9H,s), 1.54(9H,s), 1.60–1.74(1H,m), 1.84–2.13(2H,m), 2.24(1H, td,J=6,13z), 2.40(1H,dd,J=11,21 Hz), 3.31(1H,dd,J=4,11 Hz), 3.39–3.60(2H,m), 3.76–3.98(2H,m),4.13–4.55(3H,m)

Example 4

(3S)-3-[[(R)-Hydroxy-(2S,4R)-(N-tert-butoxycarbonyl-4-methanesulfonyloxy)pyrrolidin-2yl]methyl]pyrrolidin-2-one

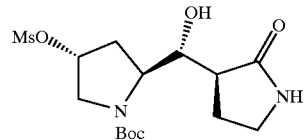

A 1.0 M solution of lithium bis(trimethylsilyl)amide (LHMDS) in tetrahydrofuran (5.2 ml, 5.2 mM) was added dropwise into a solution of (4R)-3-(4-azidobutanoyl)-4-phenyloxazolidin-2-one (1.3 g, 4.7 mM) in tetrahydrofuran (25 ml) in a nitrogen gas stream at −78° C., and the mixture was stirred at the same temperature for 30 minutes. A solution of (2S,4R)-N-tert-butoxycarbonyl-4-methanesulfonyloxypyrrolidin-2-carbaldehyde (1.8 g, 6.1 mM) in tetrahydrofuran (5 ml) was added dropwise thereinto and the mixture was stirred at the same temperature for 20 minutes. The reaction was ceased by adding dropwise a solution of acetic acid (630 mg, 9.4 mM) in tetrahydrofuran (5 ml) thereinto, and the mixture was poured into a 10% aqueous solution of citric acid followed by extracting with ethyl acetate. The organic layer was washed with water, a saturated aqueous solution of sodium bicarbonate and brine in this order and dried over anhydrous magnesium sulfate.

After concentrating the solvent, the residue was dissolved in tetrahydrofuran (30 ml), a 10% palladium-carbon (1 g) was added thereto and the mixture was subjected to a catalytic hydrogen reduction at room temperature and at 4 atmospheres pressure for 1.5 hours. The reaction mixture was filtered through Celite and the filtrate was concentrated. The residue was dissolved in 50 ml of methanol and stirred after addition of a small amount of activated charcoal. Then the mixture was filtered again through Celite. The filtrate was concentrated and the residue was subjected to a silica gel column chromatography (Wakogel C-200; hexane/ethyl acetate=1/5) to give the title compound (1.2 g, 2 steps, 67%).

Incidentally, (4R)-4-phenyloxazolidin-2-one was recovered (670 mg, 87% being recovered).

$^1$H-NMR (CDCl$_3$) δ: 1.47(9H,s), 2.00–2.26(4H,m), 2.55–2.66(1H,m), 3.04(3H,s), 3.30–3.42(2H,m). 3.56–4.08 (4H,m) 4.14(0.3H,bd,J=9 Hz), 4.25(0.7H,bd,J=9 Hz), 5.30–5.40(1H,m), 6.05(0.7H,bs), 6.18(0.3H,bs)

Example 5

(3S)-N-tert-Butoxycarbonyl-3-[[(R)-hydroxy-(2S,4R)-(N-tert-butoxycarbonyl-4-methanesulfonyloxy)pyrrolidin-2-yl]methyl]pyrrolidin-2-one

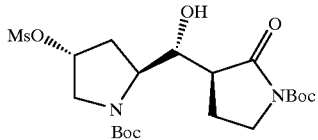

4-Dimethylaminopyridine (284 mg, 2.3 mM) and di-tert-butyl dicarbonate (507 mg, 2.3 mM) were added to a solution of (3S)-3-[[(R)-hydroxy-(2S,4R)-(N-tert-butoxycarbonyl-4-methanesulfonyloxy)pyrrolidin-2-yl]methyl]pyrrolidin-2-one (800 mg, 2.1 mM) in a 1:1 mixture (20 ml) of methylene chloride and acetonitrile, and the mixture was stirred at room temperature for 1 hour. The mixture was poured into water followed by extracting with ethyl acetate and the organic layer was washed with a saturated aqueous solution of ammonium chloride and brine in this order and dried over anhydrous magnesium sulfate. The solvent was removed to give the title compound almost quantitatively (1.01 g).

$^1$H-NMR (CDCl$_3$) δ: 1.46(9H,s), 1.53(9H,s), 1.60–1.75 (1H,m), 1.86–2.20(3H,m), 2.47(1H,dd,J=8,10 Hz), 2.50–2.62(1H,m),3.02(3H,s), 3.51–4.34(6H,m),5.24–5.36 (1H,m)

Example 6

(2S,4R)-N-tert-Butoxycarbonyl-2-[[(3R)-N-tert-butoxycarbonylpyrrolidin-3-yl-(R)-hydroxy]mehtyl]-4-methanesulfonyloxypyrrolidine

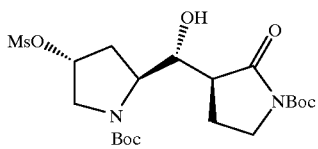

A complex (0.3 ml, 3.3 mM) of borane with dimethyl sulfide was added dropwise into a solution of (3S)-N-tert-butoxycarbonyl-3-[[(R)-hydroxy-(2S,4R)-(N-tert-butoxycarbonyl-4-methanesulfonyloxy)pyrrolidin-2-yl]methyl]pyrrolidin-2-one (500 mg, 1.1 mM) in anhydrous tetrahydrofuran (30 ml) at room temperature and the mixture was heated under reflux for one hours. The reaction mixture was ice-cooled and 10 ml of methanol was added dropwise. The solvent was removed and the residue was subjected to a silica gel column chromatography (Wakogel C-200; hexane/ethyl acetate=1/5) to give the title compound (365 mg, 75%).

$^1$H-NMR (CDCl$_3$) δ: 1.44(9H,s), 1.48(9H,s), 1.70–2.57 (5H,m), 3.04(3H,s), 3.10–3.33(2H,m), 3.45–3.70(3H,m), 3.80–4.20(3H,m), 5.21–5.38(1H,m)

Example 7

(2S,4S)-4-Acetylthio-N-tert-butoxycarbonyl-2-[[(3R)-N-tert-butoxycarbonylpyrrolidin-3-yl-(R)-hydroxy]methyl]pyrrolidine

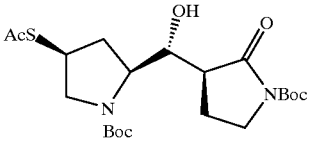

(2S,4R)-N-tert-Butoxycarbonyl-2-[[(3R)-N-tert-butoxycarbonylpyrrolidin-3-yl-(R)-hydroxy]methyl]-4-methanesulfonyloxypyrrolidine (30.1 g, 64.8 mM) was dissolved in 120 ml of anhydrous dimethylformamide, then potassium thioacetate (Wako; >90%; 12.1 g, 95 mM) was added in a nitrogen gas stream and the mixture was heated under stirring at 80° C. for 7 hours. After the reaction, the solvent was evaporated, water was added thereto and then extracted with ethyl acetate. The organic layer was washed with water and brine, and dried over anhydrous magnesium sulfate. After removing the solvent, the residue was subjected to a silica gel column chromatography (Kieselgel 60, Merck; hexane/ethyl acetate=3/20 to 1/5 to 3/10 to 2/5) to give the title compound (18.6 g, 66%).

$^1$H-NMR (CDCl$_3$) δ: 1.44(9H,s), 1.46(9H,s), 1.78–2.40 (5H,m), 2.34(3H,s), 2.98–3.33(3H,m), 3.40–4.16(6H,m)

Example 8

(2S,4S)-2-[[(3R)-Pyrrolidin-3-yl-(R)-hydroxy]methyl]-4-mercaptopyrrolidine dihydrochloride

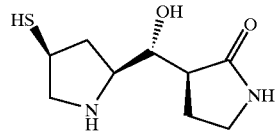

·2HCl (2S,4S)-4-Acetylthio-N-tert-butoxycarbonyl-2-[{(3R)-N-tert-butoxycarbonylpyrrolidin-3-yl-(R)-hydroxy}methyl]pyrrolidine (18.6 g, 42.8 mM) was dissolved in 186 ml of a 10% hydrochloric acid/methanol solution and then it was stirred a whole day and night at room temperature. After the reaction, the solvent was evaporated, the residue was dissolved in 800 ml of methanol and 3.72 g of activated charcoal (Shirasagi) was added thereto. After stirring for 30 minutes, the mixture was filtered and the solvent was evaporated. The residue was crystallized from diisopropyl ether/ethanol system to give the title compound (10.7 g, 93%).

$^1$H-NMR (D$_2$O) δ: 1.56–2.50(5H,m), 2.96–3.90(9H,m)

Referential Example 1

(1R,5S,6S)-6-[(R)-1-Hydroxyethyl]-1-methyl-2-
[[(2S,4S)-2-[(3R)-pyrrolidin-3-yl-(R)-hydroxy]
methyl]pyrrolidin-4-ylthio]-1-carbapen-2-em-3-
carboxylic acid acetate

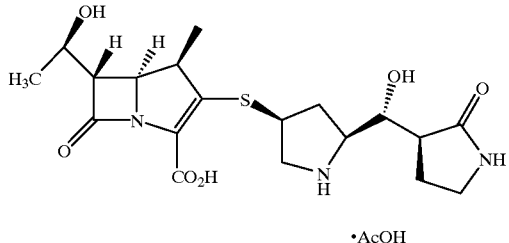

·AcOH (2S,4S)-2-[[(3R)-Pyrrolidin-3-yl-(R)-hydroxy]methyl]-4-mercaptopyrrolidine dihydrochuoride (0.55 g, 2 mM) and p-nitrobenzyl(1R,5S,6S)-2-diphenoxyphosphoryloxy-6-[(R)-1-hydroxyethyl]-1-methyl-1-carbapen-2-em-3-carboxylate (19 g, 2 mM) were dissolved in 12 ml of dimethylformamide, triethylamine (0.92 ml, 6.6 mM) was added under ice-cooling and the mixture was stirred at the same temperature for 3 hours. After evaporating the solvent, the residue was dissolved in 12 ml of tetrahydrofuran and 24 ml of 0.35 M phosphate buffer (pH: 6.0) followed by adding 2.4 g of zinc dust thereto. The mixture was stirred at room temperature for 2 hours and filtered through a GF filter paper. The filtrate was evaporated, washed with ethyl acetate and the aqueous layer was adjusted to pH 8.0 with a 1 N aqueous solution of sodium hydroxide, filtered through a Millipore and then subjected to an ODS column chromatography. The column was eluted with 3% methanol/0.06% aqueous acetic acid and the aimed fraction was concentrated and freeze-dried to give the title compound (264 mg, 26%).

$^1$H-NMR (D$_2$O) δ: 1.16(3H,d,J=7H), 1.23(3H,d,J=6 Hz), 1.65–1.78 (1H,m), 1.78–1.90(1H, m), 1,85(3H,s), 2.07–2.18 (1H,m), 2.43(1H,qd,J=9,18 Hz), 2.57(1H,td, J=8,14 Hz), 3.15(1H,dd,J=10,12 Hz), 3.20–3.36(3H,m), 3.38–3.47(2H, m), 3.50(1H,dd,J=8,12 Hz), 3.63(1H,dd,J=7,12 Hz), 3.80 (1H,ddd,J=4,8,12 Hz), 3.90–4.00(2H,m), 4.14–4.23(2H,m)

When an elution in the ODS column chromatography was carried out with water-20% aqueous solution of methanol, the aimed fraction was concentrated and the solution was adjusted to pH 6 with 1N hydrochloric acid followed by freeze-drying in the above operation, the hydrochloride of (1R,5S,6S)-6-[(R)-1-hydroxyethyl]-1-methyl-2-[[(2S,4S)-2-[(3R)-pyrrolidin-3-yl-(R)-hydroxy]methyl]pyrrolidin-4-ylthio]-1-carbapen-2-em-3-carboxylic acid was obtained as an amorphous substance.

Referential Example 2

Crystallization of (1R,5S,6S)-6-[(R)-1-hydroxyethyl]-1-methyl-2-[[(2S,4S)-2-[(3R)-pyrrolidin-3-yl-(R)-hydroxy]methyl]pyrrolidin-4-ylthio]-1-carbapen-2-em-3-carboxylic acid hydrochloride First, 100 mg of the amorphous hydrochloride was dissolved in distilled water (0.3 ml), then isopropyl alcohol (40 drops) was added thereto and the mixture was allowed to stand at 4° C. for three whole days and nights. The resulting solid was collected by filtration, and washed with a small amount of isopropyl alcohol to give a finely powdered solid. This solid was found to be crystals as a result of a powder X-ray diffractometry.

Then, 5.1 g of the amorphous hydrochloride was dissolved in distilled water (55 ml) and ethanol (300 ml) was added thereto under ice-cooling. The solution was returned to room temperature and ethanol (10 ml) was added dropwise thereinto little by little. The previously-prepared crystals were seeded to the resulting white solution and stirred at room temperature for 5 minutes. Ethanol (50 ml) was added thereto during 20 minutes in 5 portions, then ethanol (140 ml) was further added thereto under ice-cooling during 10 minutes and the mixture was stirred at the same temperature for 25 minutes. The resulting crystals were collected by filtration, washed with cold ethanol, air-dried for one whole day and night and dried in vacuo for five whole days and nights to give white crystals (4.55 g).

m.p. 192° (decomp.)

$^1$H-NMR (D$_2$O) δ: 1.17(3H, d, J=7H), 1.24(3H, d, J=6 Hz), 1.73 (1H,qd, J=9,13 Hz), 1.84 (1H, ddd, J=7,10,12 Hz), 2.07–2.18(1H, m), 2.44 (1H, qd, J=9,18 Hz), 2.58(1H,td,J= 8,14 Hz), 3.15 (1H, dd, J=10,12 Hz), 3.21–3.37(3H,m), 3.39–3.47(2H, m), 3.51(1H, dd, J=8,12 Hz), 3.64 (1H, dd, J=7,12 Hz), 3.83(1H, ddd, J=3,8,11 Hz), 3.92–4.01 (2H,m), 4.15–4.23(2H,m) $[α]_D^{24.2}$+8.41° (C=1.01, H$_2$O) HPLC purity: 99.6% (Shimadzu Liquid Chromatograph LC-6A; a column for industrial analysis by a gas chromatography, Inertsil ODS-2 (lot ODI 10157), Shimadzu UV Spectrophotometric Detector SPD-6A; wavelength: 294 nm; flow rate: 1.0 ml/min; 10% MeOH-0.1% AcONH$_4$—H$_2$O or 20% MeOH-0.1% AcONH$_4$-H$_2$O).

The effect of the present invention will be compared with that of the prior art.

In the step 1 in the method disclosed in Drugs of the Future, 1996, 21 (4): 361–365 or JP-A 8-73462 and the step A to step B in the present invention, one of the starting materials is the same or nearly the same, and the products are the same (with to difference that an NH group in the resulting lactam ring has a protecting group or not) and, therefore, those steps will be compared.

The step 1 is shown in Production Example 6 of JP-A 8-73462 and the diastereomer B has the aimed configuration. The yield of this diastereomer B, i.e. (3S)-3-[[(R)-hydroxy-(2S,4R)-(N-tert-butoxycarbonyl-4-tert-butyldimethylsilyloxy)pyrrolidin-2-yl]methyl]-N-tert-butoxycarbonylpyrrolidin-2-one, is mentioned to be 30.2%.

On the other hand, the specific examples in the step A to step B in the present invention corresponding to the above diastereomer B are Examples 1 and 2 showing the method for the manufacture of (3S)-3-[[(R)-hydroxy-(2S,4R)-(N-tert-butoxycarbonyl-4-tert-butyldimethylsilyoxy)pyrrolidin-2-yl]methyl]pyrrolidin-2-one having no protecting group for an NH group in the resulting lactam ring, and Example 4 showing the method for the manufacture of (3S)-3-[[(R)-hydroxy-(2S,4R)-(N-tert-butoxycarbonyl-4-methanesulfonyloxy)pyrrolidin-2-yl]methyl]pyrrolidin-2-one where the substituent is partially different and, their yields are 63% (in two steps) and 67%, respectively. That is, in accordance with the method of the present invention, the yield for the manufacture of the compounds having the desired stereostructure is improved to an extent of about two-fold as compared with the conventional method.

As such, as compared with the conventional method, the present invention has the following advantages.

1) the yield is about doubled; and
2) expensive optically active substances, i.e. (2S,4R)-pyrrolidine-2-carbaldehyde compounds, can be utilized without loss.

In order to give the desired configuration, (4R)-4-phenyloxazolidin-2-one, etc. are now necessary, but they are able to be recovered and recycled.

What is claimed is:

1. A (4R)-[3-[2-(ω-substituted alkyl)-3-(R)-hydroxy-1-oxo-3-(2S,4R)-2-pyrrolidinyl]propyl]-oxazolidin-2-one (or thiazolidine-2-thione) compound represented by the formula (I):

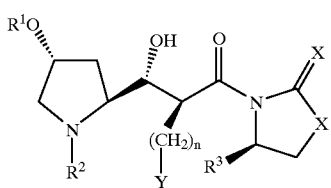

wherein $R^1$ is selected from the group consisting of methylsulfonyl, ethylsulfonyl, propylsulfonyl, phenylsulfonyl, p-toluenesulfonyl, trimethylsilyl, triethylsilyl, isopropyldimethylsilyl, t-butyldimethylsilyl, t-butyldiphenylsilyl and vinyldimethylsilyl; $R^2$ is a protecting group selected from the group consisting of formyl, acetyl, chloroacetyl, dichloroacetyl, propionyl, phenylacetyl, thienylacetyl, t-butoxycarbonyl, benzyloxycarbonyl, p-nitrobenzyloxycarbonyl, p-methoxybenzyloxycarbonyl, p-bromobenzyloxycarbonyl and 2,4-dichlorobenzyloxycarbonyl; $R^3$ is a substituted or unsubstituted lower alkyl group or an aryl group; X is an oxygen atom or a sulfur atom; Y is an azide group or a nitro group; and n is an integer of 1 to 4.

2. The compound as claimed in claim 1, wherein X is an oxygen atom.

3. The compound as claimed in claim 1, wherein Y is an azide group.

4. The compound as claimed in claim 1, wherein n is 2.

* * * * *